US00PP22968P2

(12) United States Plant Patent
Egger

(10) Patent No.: US PP22,968 P2
(45) Date of Patent: Aug. 14, 2012

(54) ***KNIPHOFIA* PLANT NAMED 'MANGO POPSICLE'**

(50) Latin Name: ***Kniphofia* spp.**
Varietal Denomination: Mango Popsicle

(75) Inventor: Janet N. Egger, Wilsonville, OR (US)

(73) Assignee: Terra Nova Nurseries, Inc., Canby, OH (US)

( * ) Notice: Subject to any disclaimer, the term of this patent is extended or adjusted under 35 U.S.C. 154(b) by 0 days.

(21) Appl. No.: 13/066,147

(22) Filed: Apr. 6, 2011

(51) Int. Cl.
*A01H 5/00* (2006.01)

(52) U.S. Cl. ..... Plt./443

(58) Field of Classification Search ..... Plt./443
See application file for complete search history.

*Primary Examiner* — Annette Para

(74) *Attorney, Agent, or Firm* — Klarquist Sparkman, LLP

(57) ABSTRACT

A new and distinct *Kniphofia* plant characterized by its very early blooming, repeat blooming, compact habit with multiple crowns, narrow, grassy leaves, glowing, yellow orange flowers, and excellent vigor.

1 Drawing Sheet

Botanical denomination: *Kniphofia* spp.
Cultivar designation: Mango Popsicle.

BACKGROUND OF THE INVENTION

The present invention relates to a new and distinct *Kniphofia*, and given the cultivar name is 'Mango Popsicle'. *Kniphofia* is in the family Asphodelaceae. 'Mango Popsicle' is a hybrid resulting from a planned breeding program to produce compact, reblooming *Kniphofia*. The cross was made using the following proprietary, unreleased plants: *Kniphofia* 10-1, as the seed parent, and *Kniphofia* 10-2, as the pollen parent. It was selected for best habit, flower color, reblooming, and crown count from many seedlings of the cross in Canby, Oreg.

Compared to *Kniphofia* 'Bressingham Comet' (an unpatented plant), the seed parent, the new cultivar is more free flowering with yellow orange flowers rather than yellow to red orange flowers.

Compared to *Kniphofia* 'Papaya Popsicle' (U.S. Plant patent application Ser. No. 13/066,135), the new cultivar is taller with yellow orange rather than red orange flowers.

SUMMARY OF THE INVENTION

The new cultivar is unique and characterized by:

1. very early blooming (flowers the first year in 30 cell plugs)
2. repeat blooming from June through September in Canby, Oreg.
3. compact habit with multiple crowns
4. narrow, grassy leaves
5. glowing, yellow orange flowers
6. excellent vigor This new cultivar has been reproduced only by asexual propagation (division, tissue culture). Each of the progeny exhibits identical characteristics to the new cultivar. Asexual propagation by leaf cuttings, tissue culture, and division using standard techniques as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a plant of a one-year-old *Kniphofia* 'Mango Popsicle' in the ground in the trial field in May in Canby, Oreg.

DETAILED PLANT DESCRIPTION

The following is a detailed description of the new *Kniphofia* cultivar based on observations 32 cell size, six month old specimens grown from tissue culture, grown outside in part sun in Canby, Oreg. The color descriptions are all based on The Royal Horticultural Society Colour Chart, 5$^{th}$ edition.

Plant:
- *Type*.—Rhizomatous herbaceous perennial.
- *Hardiness*.—USDA Zones 6 to 9.
- *Size*.—Grows to 41 cm wide and 34 cm tall from the top of the soil to the top of the foliage.
- *Form*.—Upright and clumping.

Leaf:
- *Type*.—Simple.
- *Shape*.—Strap-like.
- *Arrangement*.—Basal rosette.
- *Blade size*.—Grows to 40 cm long and 12 mm wide.
- *Margins*.—Entire.
- *Apex*.—Acuminate.
- *Base*.—Clasping.
- *Surface texture*.—Glabrous on both surfaces.
- *Venation*.—Parallel.
- *Color*.—Top and bottom side Green 137A.

Inflorescence:
- *Type*.—Spike-like scapose raceme.
- *Number of flowers per raceme*.—About 120.
- *Inflorescence*.—13 cm long and 5 cm wide.
- *Peduncle description*.—Grows to 50 cm long and 7 mm wide, glabrous to glaucous, Yellow Green 146C.
- *Pedicle description*.—2.5 mm long, glabrous, Yellow Green N144A.

*Bloom time*.—June through September in Canby, Oreg.

*Lastingness*.—An inflorescence lasts for 2 to 4 weeks depending on the temperatures.

Flower bud:

*Size*.—28 mm long and 4 mm wide.

*Shape*.—Cylindrical.

*Surface texture*.—Glabrous.

*Color*.—Orange 25B on top, Yellow Orange 19A on bottom, and Yellow 11B at base.

Flower:

*Type*.—Actinomorphic.

*Shape*.—Cylindrical and tubular.

*Size*.—Grows to 3 cm deep and 10 mm wide.

*Texture*.—Waxy.

*Surface texture*.—Glabrous inside and outside.

*Color*.—Inside and out: Yellow Orange 23A on top ¾ and Yellow Orange 18A on bottom ¾, with Yellow 8A on end nearest the stem.

*Corolla description*.—6 lobed fused tepals, 3 cm long and 1 cm wide, tube 27 mm long and 5 mm wide, lobes reflex 3 mm wide and 4 mm long, ovate, entire, obtuse to acute, inside and out glabrous and Yellow Orange 23A on top ¾ and Yellow Orange 18A on bottom ¾, with Yellow 8A on end nearest the stem.

*Pistil description*.—One extruding, 4 cm long, ovary 4 mm long 2.5 mm wide, Yellow Green 144A, style 37 mm long, Yellow Orange 15B at tip lightening to Yellow 11B at base, stigma White NN155A.

*Stamen*.—6, 22 mm long, filaments 21 mm long, and White NN155A, anthers 1 mm long and Yellow 11A, pollen none.

*Fragrance*.—None.

Fruit and seed: None seen.

Pest and diseases: Pests and diseases are infrequent on *Kniphofia* spp. No problems have been observed on this plant grown under commercial conditions in Canby, Oreg.

I claim:

1. A new and distinct *Kniphofia* plant as herein shown and described.

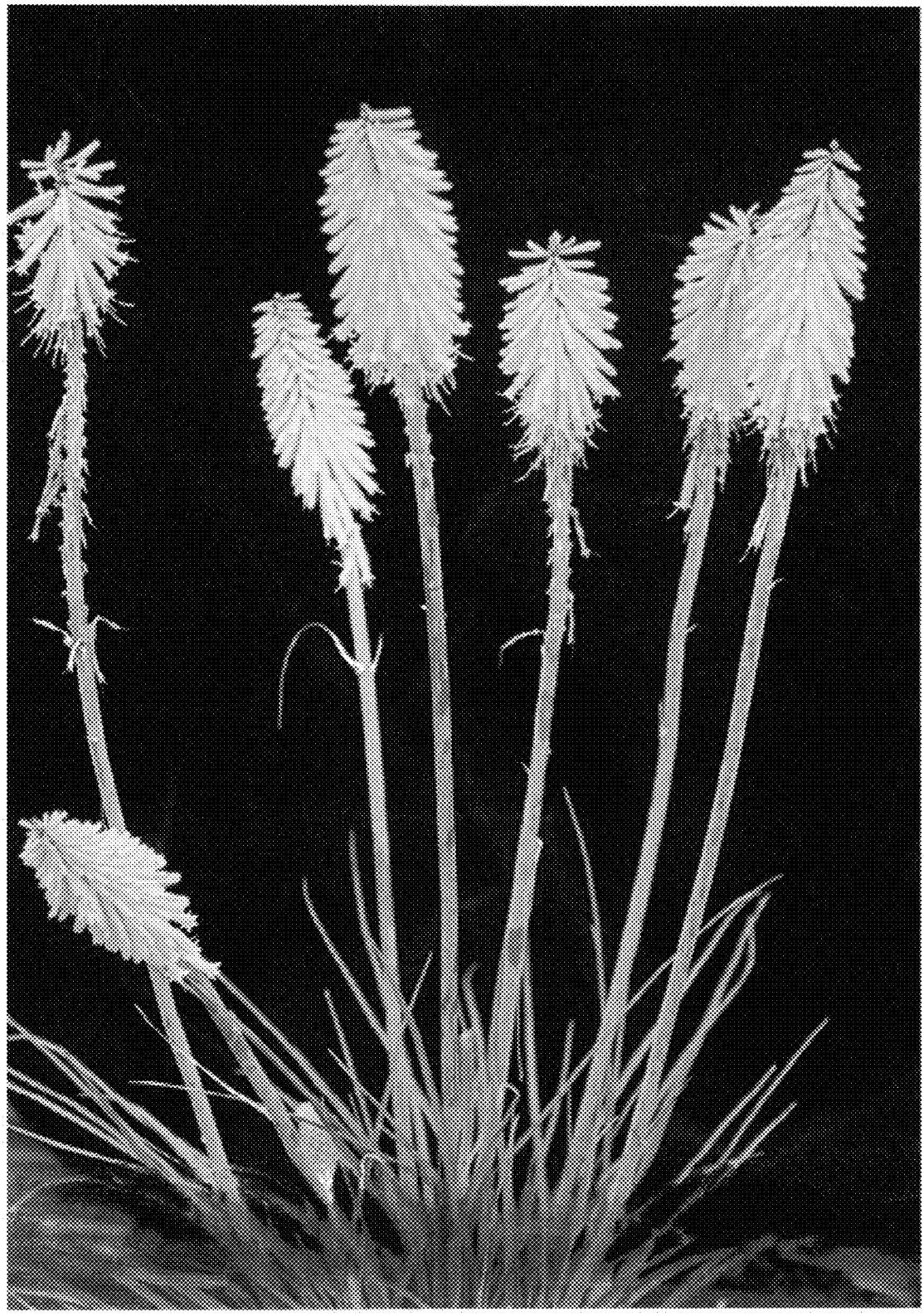

* * * * *